(12) United States Patent
Mirvakili et al.

(10) Patent No.: US 10,935,008 B2
(45) Date of Patent: Mar. 2, 2021

(54) MULTIDIRECTIONAL ARTIFICIAL MUSCLES FROM NYLON

(71) Applicant: Massachusetts Institute of Technology, Cambridge, MA (US)

(72) Inventors: Seyed M. Mirvakili, Vancouver (CA); Ian W. Hunter, Lincoln, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/345,183

(22) PCT Filed: Oct. 26, 2016

(86) PCT No.: PCT/US2016/058767
§ 371 (c)(1),
(2) Date: Apr. 25, 2019

(87) PCT Pub. No.: WO2018/080465
PCT Pub. Date: May 3, 2018

(65) Prior Publication Data
US 2019/0285060 A1 Sep. 19, 2019

(51) Int. Cl.
*F03G 7/06* (2006.01)
*A61B 34/00* (2016.01)
(Continued)

(52) U.S. Cl.
CPC ............... *F03G 7/06* (2013.01); *A61B 34/76* (2016.02); *A61F 2/08* (2013.01); *A61M 25/0116* (2013.01);
(Continued)

(58) Field of Classification Search
CPC .. F03G 7/06; F03G 7/00; F03G 7/005; A61M 25/0116; A61B 34/76; C08G 69/00;
(Continued)

(56) References Cited

U.S. PATENT DOCUMENTS 3,719,551 A * 3/1973 Radtke ..................... B21B 3/00
428/213
6,372,951 B1 * 4/2002 Ter-Ovanesyan ...........................
A61B 5/04884
600/373
(Continued)

FOREIGN PATENT DOCUMENTS

WO 2015140149 A1 9/2015

OTHER PUBLICATIONS

Yoshino, T. et al, "Three-Dimensional Photomobility of Crosslinked Azobenzene Liquid-Crystalline Polymer Fibers," Advanced Materials, vol. 22, 2010, pp. 1361-1363.
(Continued)

*Primary Examiner* — Hoang M Nguyen
(74) *Attorney, Agent, or Firm* — Sunstein LLP (57) ABSTRACT

A bending actuator and methods for making and using the same. A beam of anisotropic polymer material, such as nylon, characterized by a greater degree of molecular orientation along a longitudinal axis than transverse to the longitudinal axis, has a heating element in thermal contact with at least one of a pair of opposing faces parallel to the longitudinal axis of the beam. The heating element in certain embodiments provides for photothermal activation of the bending actuator.

15 Claims, 9 Drawing Sheets

(51) Int. Cl.
  *A61M 25/01* (2006.01)
  *B29C 71/02* (2006.01)
  *B81B 3/00* (2006.01)
  *C08G 69/00* (2006.01)
  *C09K 5/14* (2006.01)
  *G01B 7/16* (2006.01)
  *A61F 2/08* (2006.01)
  *F03G 7/00* (2006.01)
  *B29L 31/00* (2006.01)

(52) U.S. Cl.
  CPC ............ *B29C 71/02* (2013.01); *B81B 3/0024* (2013.01); *C08G 69/00* (2013.01); *C09K 5/14* (2013.01); *F03G 7/005* (2013.01); *G01B 7/18* (2013.01); *A61F 2002/0894* (2013.01); *B29C 2071/022* (2013.01); *B29L 2031/749* (2013.01); *B81B 3/0062* (2013.01); *B81B 2201/032* (2013.01); *F03G 7/00* (2013.01)

(58) Field of Classification Search
  CPC ..... C09K 5/14; G01B 7/18; A61F 2002/0894; A61F 2/08; B29C 2071/022; B29C 71/02; B81B 2201/032; B81B 3/0062; B81B 3/0024; B29L 2031/749
  USPC .............................. 310/306–307; 60/527–529
  See application file for complete search history.

(56) References Cited

U.S. PATENT DOCUMENTS

| | | | |
|---|---|---|---|
| 6,628,040 B2 * | 9/2003 | Pelrine | F02G 1/043 310/307 |
| 7,008,675 B2 | 3/2006 | Kornfield et al. | |
| 2004/0122174 A1 | 6/2004 | Mather et al. | |
| 2004/0263028 A1 * | 12/2004 | Pei | F04B 35/00 310/307 |
| 2009/0317852 A1 * | 12/2009 | Parker | G01N 33/5061 435/29 |
| 2010/0141085 A1 * | 6/2010 | Wu | H01M 8/1051 310/311 |
| 2010/0171393 A1 * | 7/2010 | Pei | H01L 41/0986 310/330 |
| 2012/0073388 A1 * | 3/2012 | Chibante | G01L 1/20 73/862.627 |
| 2014/0238488 A1 * | 8/2014 | Jiang | F24S 30/48 136/259 |
| 2015/0005407 A1 | 1/2015 | Basfar et al. | |

OTHER PUBLICATIONS

International Search Report and Written Opinion, prepared by Korean Intellectual Property Office, dated Jul. 24, 2017 (13 pages).

* cited by examiner

FIG. 11

MULTIDIRECTIONAL ARTIFICIAL MUSCLES FROM NYLON

CROSS-REFERENCE TO RELATED APPLICATIONS

This application is the national phase entry of international patent application no. PCT/US2016/058767 filed Oct. 26, 2016, the disclosure of which is incorporated herein by reference in its entirety.

TECHNICAL FIELD

The present invention relates to bending actuators and methods for manufacturing them, and, more particularly, to thermally activated polymer bending actuators.

BACKGROUND ART

Artificial muscles are materials or devices that can reversibly contract, expand, or rotate within a single integral structure due to an external stimulus (such as voltage, current, pressure or temperature). Performance metrics of artificial muscles include cycle life, gravimetric/volumetric energy and/or power density, efficiency, cost, and controllability.

Enhancing such performance characteristics of artificial muscles has been an active field of research and has encompassed such materials as conducting polymers, dielectric elastomers, carbon nanotubes and graphene, to list a number of examples. Polymers are macromolecules made up of identical or similar monomers joined covalently into a chain. Various polymer actuators have been studied both for linear (tensile) application and for bending. For example, conductive polymer bending actuators are described in John, et al., "*Towards the position control of conducting polymer trilayer bending actuators with integrated feedback sensor,*" *IEEE/ASME International Conference on Advanced Intelligent Mechatronics*, pp. 65-70 (2009), which is incorporated herein by reference. Actuation in conductive polymers, more generally, is reviewed by Kaneto, "*Research Trends of Soft Actuators based on Electroactive Polymers and Conducting Polymers.*" *Journal of Physics: Conference Series*, vol. 704, No. 1, (2016), incorporated herein by reference. Actuation may also be achieved in shape-memory polymers, as reviewed by Liu, et al., "*Shape memory polymers and their composites in aerospace applications: a review,*" *Smart Materials and Structures*, vol. 23, (2014): 023001, which is also incorporated herein by reference. Other existing actuation technologies involving polymers include fiber-reinforced or carbon-nanotube hybrid configurations.

Yet, few artificial muscles provide a satisfactory combination of the performance parameters mentioned above. For example, although shape memory alloys can provide high contractile stress (200-480 MPa), their poor cycle life (<1000 cycles) at high tensile strains, high cost (300 $/kg), low efficiency, and difficult controllability limit their applications. Conducting polymers offer contractile stresses of 2-120 MPa and require low excitation voltage (<4 V), but they are slow, suffer from low electrochemical coupling, and also scalability of their produced force in the current generation of small film actuators is on the order of few mN. The recently discovered miniature linear and torsional artificial muscles fabricated from carbon nanotube yarns and nanowire yarns offer long cycle life (>1 million cycles), but their manufacturing cost is not low enough for commercialization yet.

Nylon is a material that has been used as an actuator material, however only for linear actuation applications, where the highly anisotropic material is twisted about the actuation axis.

Prior art thermally powered polymer bending actuators have never been free-standing but have been only been formed by encapsulating a metal tab inside a Parylene-C coating, as described in Chan et al., "*A Thermally Activated Polymer Micro Robotic Gripper for Manipulation of Biological Cells,*" Robotics and Automation, Proc. IEE Int. Conf. on Robotics and Automation, pp. 288-93 (2003), which is incorporated herein by reference.

It would be desirable to achieve bending in a thermally actuated polymer without requiring an encased metal. A free-standing thermally activated polymer bending actuator is provided for the first time in accordance with the present invention, as described below.

SUMMARY OF EMBODIMENTS OF THE INVENTION

In accordance with embodiments of the invention, a bending actuator is provided that has a beam of anisotropic polymer material. The beam of anisotropic polymer material is characterized by a greater degree of molecular orientation along a longitudinal axis than transverse to the longitudinal axis, and by a substantially polygonal-cross section taken in any plane transverse to the longitudinal axis. The bending actuator also has a heating element in thermal contact with at least one of a pair of opposing faces parallel to the longitudinal axis of the beam.

In accordance with other embodiments of the invention, the anisotropic polymer may be nylon and the substantially polygonal cross section may be substantially rectangular. A distinct Joule heating element may be in thermal contact respectively with each of two opposing faces of the beam of anisotropic polymer material.

In accordance with another aspect of the present invention, a method is provided for applying a force transverse to a longitudinal axis of an actuator. The method has steps of:
providing a beam of anisotropic polymer characterized by a greater degree of molecular orientation along a longitudinal axis than transverse to the longitudinal axis, and by a substantially polygonal-cross section taken in any plane transverse to the longitudinal axis;
applying a heating element to at least one of a pair of opposing faces parallel to the longitudinal axis of the beam; and
causing bending of the beam by differentially heating at least a first face of the pair of opposing faces with respect to a second face of the pair of opposing faces by Joule heating.

In other embodiments, the anisotropic polymer may be nylon, and forming the beam may include roller-pressing the anisotropic polymer. The substantially polygonal cross section may be substantially rectangular. Applying a Joule heating element to at least one face may include applying a Joule heating element to two opposing faces of the beam of anisotropic polymer.

In accordance with another aspect of the present invention, a method of manufacture of a bending actuator is provided, having steps of:
forming a beam of anisotropic polymer characterized by a greater degree of molecular orientation along a longitudinal axis than transverse to the longitudinal axis, and by a substantially polygonal-cross section taken in any plane transverse to the longitudinal axis; and applying a Joule heating element to at least one of a pair of opposing faces parallel to the longitudinal axis of the beam.

In alternate embodiments of the present invention, the anisotropic polymer may be nylon, and forming the beam may include roller-milling the anisotropic polymer. The substantially polygonal cross section may be substantially rectangular. Moreover, applying a Joule heating element to at least one face may include applying a Joule heating element to two opposing faces of the beam of anisotropic polymer, and applying a Joule heating element to at least one face may also include applying a conductive paint to the at least one face. Applying a Joule heating element to at least one face may also include applying nichrome wire to the at least one face.

In accordance with a further aspect of the present invention, a method for applying a force transverse to a longitudinal axis of an actuator is provided. The method has steps of:
  providing a beam of anisotropic polymer characterized by a greater degree of molecular orientation along a longitudinal axis than transverse to the longitudinal axis, and by a substantially polygonal-cross section taken in any plane transverse to the longitudinal axis; and
  causing bending of the beam by differentially photothermally heating at least one face of the pair of opposing faces with respect to a second face of the pair of opposing faces.

In other embodiments, differentially photothermally heating at least one face may include irradiating the at least one face with a source of light, such as a laser. Differentially photothermally heating at least one face may include irradiating a first face with a first laser and a second face with a second laser. Where the beam exhibits a catch state, the method may also have a step of returning the actuator to a neutral condition by applying heat to the cooler of the opposing faces.

In accordance with another aspect of the present invention, a method of manufacture of a bending actuator is provided. The method has steps of:
  forming a beam of anisotropic polymer material polygonal-cross section; and
  photosorptively treating at least one of opposing faces of the beam of anisotropic polymer.

In other embodiments, photosorptively treating may include applying a coating of thermally conductive paint solution that may include thermally conductive graphene flakes.

In accordance with another aspect of the present invention, a method of manufacture of a bending actuator is provided having steps of:
  providing a beam of anisotropic polymer characterized by a greater degree of molecular orientation along a longitudinal axis than transverse to the longitudinal axis, and by a substantially polygonal-cross section taken in any plane transverse to the longitudinal axis;
  annealing the beam of anisotropic polymer at a temperature between 20° C. above glass temperature of the anisotropic polymer and 20° C. below melting point of the anisotropic polymer in such a manner as to create a catch state at a specified fractional amplitude of bending; and
  treating at least one face of the beam for thermal activation.

In further embodiments, the beam of anisotropic polymer may be annealed at a temperature between 60° C. and 150° C., and providing the beam of anisotropic polymer includes roller-pressing a length of anisotropic polymer filament through a rolling mill. Treating the at least one face of the beam may include depositing a conductive trace for Ohmic heating or photosorptive treatment. Treating the at least one face of the beam may include applying heating traces to a plurality of distinct pairs of faces to achieve multidirectional actuation, and the plurality of distinct pairs of faces of the beam may be substantially orthogonal to each other.

In accordance with an alternate aspect of the present invention, a method is provided for monitoring transverse displacement amplitude of a bending actuator. The method has steps of:
  applying a conductive loop to a surface of the bending actuator; and
  monitoring resistance of the conductive loop.

In accordance with a further aspect of the present invention, an actuator for haptic feedback is provided that has a beam of anisotropic polymer characterized by a greater degree of molecular orientation along a longitudinal axis than transverse to the longitudinal axis, and by a substantially polygonal-cross section taken in any plane transverse to the longitudinal axis. The actuator also has a heating element in thermal contact with at least one of a pair of opposing faces parallel to the longitudinal axis of the beam and a controller adapted to activate the heating element and thereby apply a force capable of being sensed by skin of a person.

In accordance with yet a further aspect of the present invention, a propeller for vascular navigation is provided that has a beam of anisotropic polymer coupled to a particle, the beam characterized by a greater degree of molecular orientation along a longitudinal axis than transverse to the longitudinal axis, and by a substantially polygonal-cross section taken in any plane transverse to the longitudinal axis. The propeller also have a heating element in thermal contact with at least one of a pair of opposing faces parallel to the longitudinal axis of the beam; and a controller adapted to activate the heating element and thereby apply a force for propelling the particle through a lumen.

BRIEF DESCRIPTION OF THE DRAWINGS

The foregoing features of the invention will be more readily understood by reference to the following detailed description, taken with reference to the accompanying drawings, in which:

FIG. 3A is a schematic depiction of a polymer bending actuator fabricated by application of a heater to an anisotropic polymer beam, while

DETAILED DESCRIPTION OF EMBODIMENTS OF THE INVENTION

Definitions: A "filament," as the term is used herein and in any appended claims, is a structure characterized by a length that is at least an order of magnitude and a half longer than any transverse dimension.

The term "anisotropic," as used in reference to a solid material, herein and in any appended claims, shall denote that one or more vector or tensor intrinsic physical quantity associated with the material assumes a value along one direction that differs from the same quantity along some other direction by a factor exceeding two. The physical quantity concerned may be a coefficient of thermal expansion, a modulus of elasticity, or any other intrinsic physical quantity. An "intrinsic" physical quantity is one associated with the material itself, and is independent of physical dimensions, for example.

The term "molecular orientation" shall refer to the alignment of molecular chains in a polymer upon crystallization or partial crystallization of the polymer. Molecular orientation may exist to greater or lesser degree with respect to distinct axes of a polymer. Polymers lacking molecular orientation may be referred to herein as "randomly oriented."

The term "Joule heating" shall refer to heating of an electrical conductor by passage of an electrical current therethrough. Joule heating may be referred to herein as Ohmic heating or resistive heating, both of which terms are synonymous with Joule heating for purposes of the present description and any appended claims.

A polymer may contain regions in a crystalline or semi-crystalline phase, and regions in a solid amorphous phase. The "glass transition temperature," as the term is used herein, refers to the phase transition temperature between a crystalline or semi-crystalline phase and a solid amorphous phase. The "melting point" refers to the temperature associated with a particular polymer at which, on cooling, the polymer passes from a viscous liquid to a brittle, amorphous solid.

A "beam," as the term is used herein, is a structural element, of either homogeneous or heterogeneous composition, having a longitudinal dimension, referred to as a "length," measured along a length axis designated as $\hat{z}$, that exceeds at least one dimension transverse to the length axis by at least a factor of three. It is to be understood that the support of the beam, whether cantilevered or supported at two or more positions along the length axis, is not limited within the scope of the present invention.

A "drawn" polymer is a polymer that has been stressed in at least one direction by tensile force.

A "rolled" polymer has been passed through one or more pairs of rolls to reduce at least one dimension transverse to a length dimension.

A "highly drawn" polymer is defined as a polymer that has been drawn with a draw ratio greater than 5, where the draw ratio is defined as the ratio of a length of a line inscribed on the surface of the polymer after drawing to the length of the same line prior to drawing of the polymer.

Figure 1A:
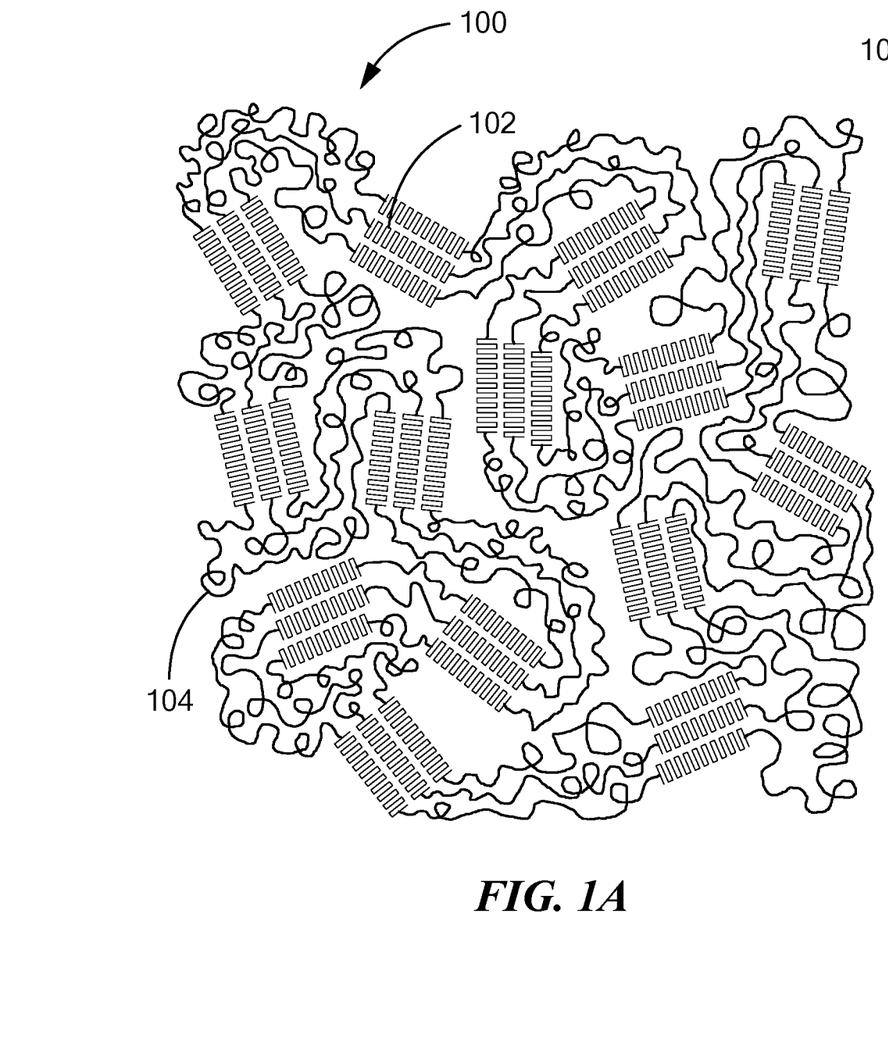
FIGS. 1A and 1B schematically depict amorphous and crystalline regions of a randomly oriented semi-crystalline polymer and a highly drawn polymer, respectively.
Figure 1B:
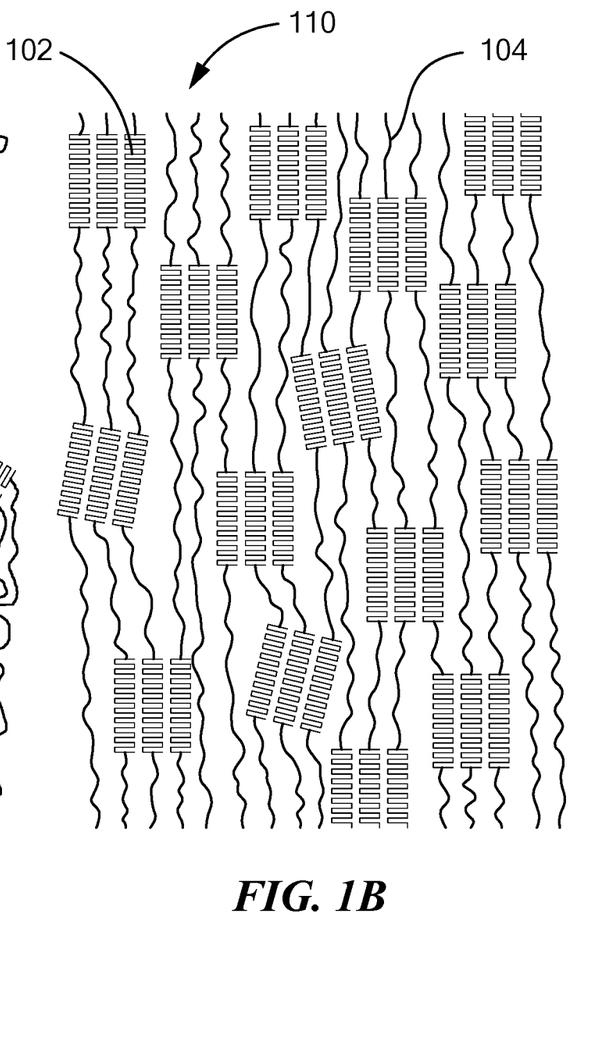

The distribution of chains in semi-crystalline structures, such as nylon, plays an important role in shaping anisotropic thermomechanical properties, as now discussed with reference to FIGS. 1A-1C. For randomly distributed chains of a polymer filament, designated generally by numeral 100 in FIG. 1A, crystalline phase regions 102 and amorphous phase regions 104 are randomly oriented. Crystalline phase regions 102 may also be referred to herein as crystalline blocks. However, for highly drawn polymer filaments, designated generally by numeral 110 in FIG. 1B, the crystalline phase regions 102 and amorphous phase regions 104 are oriented along the length of the filament. Compared to the crystalline regions 102, the amorphous regions 104 are less energetically stable. Therefore, when their thermal energy is augmented, they undergo structural changes which involve pulling the crystalline blocks 102. This structural change can lead to a negative thermal expansion coefficient in the highly drawn polymers 102. The thermal expansion of the crystalline blocks 102 causes expansion perpendicular to axis 112 of draw.

In accordance with embodiments of the present invention, an anisotropic polymer bending actuator, designated generally by numeral 120, is now described with reference to FIG. 1C. Anisotropic polymer bending actuator 120 may also be referred to herein as a "nylon bending actuator" or a "bending actuator" for ease of reference and without limiting intent.

A heating element 124 is in thermal contact with a beam 122 of anisotropic polymer material. Beam 122 is characterized by a greater degree of molecular orientation along longitudinal axis $\hat{z}$ than along any direction transverse to longitudinal axis $\hat{z}$. Heating element 124 may have conductive traces on one or more surface; middle, as in the embodiment shown in FIG. 1C. Other heating elements are within the scope of the present invention, as discussed in detail below. The zoomed-in illustration shows highly aligned crystalline regions 102 of the anisotropic polymer beam 122, while a further zoomed-in illustration to the right depicts molecular structure 129 of nylon 6,6, which is an example of a material composition of anisotropic polymer beam 122. A heating element may also be referred to herein as a "heater."

Figure 2A:
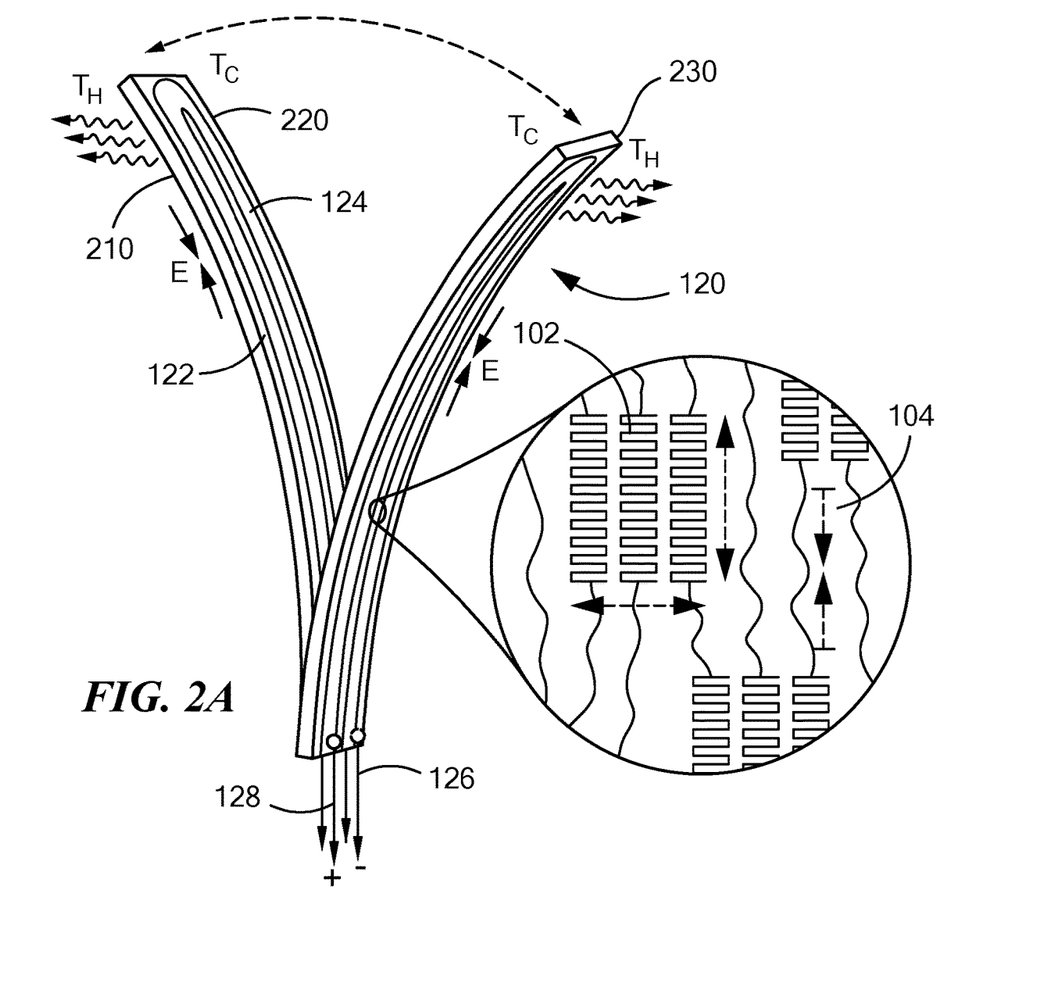
FIG. 2A shows a polymer bending actuator, in accordance with an embodiment of the present invention, with heaters applied to respective sides of the actuator. Aligned semi-crystalline regions are shown in the inset.

Bending actuator 120 is also depicted in FIG. 2A, to be discussed in greater detail below. An electrical potential difference is applied between leads 126 and 128 to cause a flow of current in heating element 124 and thus to bending of anisotropic polymer beam 122. Surfaces of beam 122 that are respectively relatively hotter and cooler are designated $T_H$ and $T_C$.

Further description of certain embodiments of a nylon bending actuator may be found in Mirvakili et al., "*Bending Artificial Muscle from Nylon Filaments,*" *Electroactive Polymer Actuators and Devices (EAPAD), Proc. SPIE*, vol. 9798, 97981L1-L7 (presented Mar. 23, 2016), which is incorporated herein by reference.

Figure 3A:
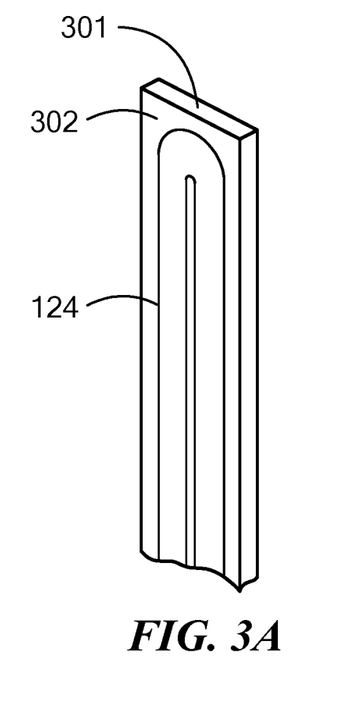

Referring now to FIG. 3A, fully reversible bending in one plane (either of X or Y, orthogonal planes intersecting in longitudinal axis $\hat{z}$) may be achieved upon heating of rectangular-cross section nylon beams 301 by heating element 124. (It is to be recalled that heating elements are depicted herein as Joule heating loops by way of example only, and that any heating element is within the scope of the present invention, as further discussed below. Similarly, "nylon" is to be understood as a non-limiting example of an anisotropic polymer.)

Figure 3B:
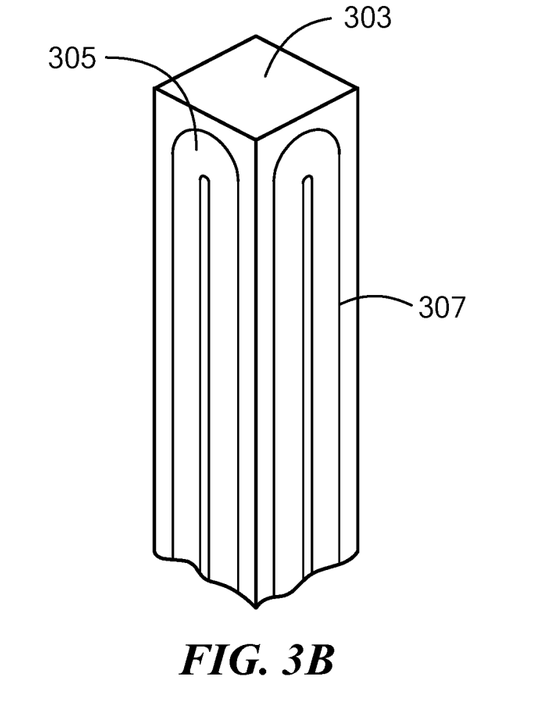
FIG. 3B is a schematic depiction of a multidirectional polymer bending actuator fabricated by application of a heater to non-opposing faces of an anisotropic polymer rod with a polygonal cross-section, in accordance with another embodiment of the present invention. (Heaters applied to opposing faces of the rod are not shown.)

As shown in FIG. 3B, nylon square rods 303 enable 2D bending (concurrently in XY planes) when heat is applied, by heaters 305 and 307, to different sides of square rod 303. Extension to rods having substantially polygonal cross sections, such as substantially rectangular cross sections, is within the scope of the present invention.

Figure 4:
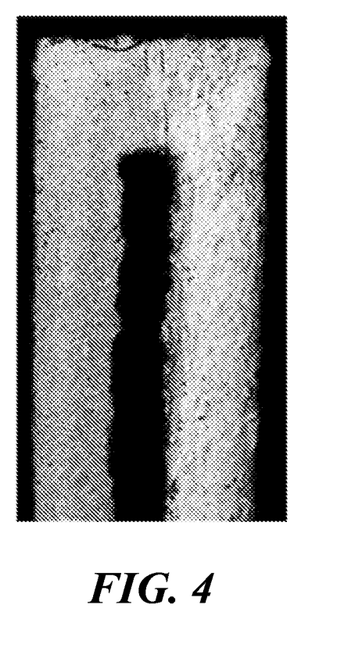
FIG. 4 is a scanning electron microscope (SEM) image of a patterned conductive coating on a nylon beam in accordance with an embodiment of the present invention.

Heat for actuation may be generated by any means, within the scope of the present invention. Examples include Joule heating, as depicted in FIGS. 3A-3B, or radiative heating, which may be referred to synonymously herein as photo-thermal heating. To create the Joule heating traces 124, 305 and 307 on surfaces 302 of the nylon beams 301, 303, a conductive paint is applied that is a colloidal suspension of micron-size silver flakes mixed with metallic nanowires, such as niobium, in an adhesive resin. Any conductive paint used for Joule heating traces is encompassed within the scope of the present invention, including, for example, any type of highly conductive nanowires with lengths, for example, of several mm. A scanning electron microscope (SEM) image of the patterned conductive coating is shown in FIG. 4.

Figure 2B:
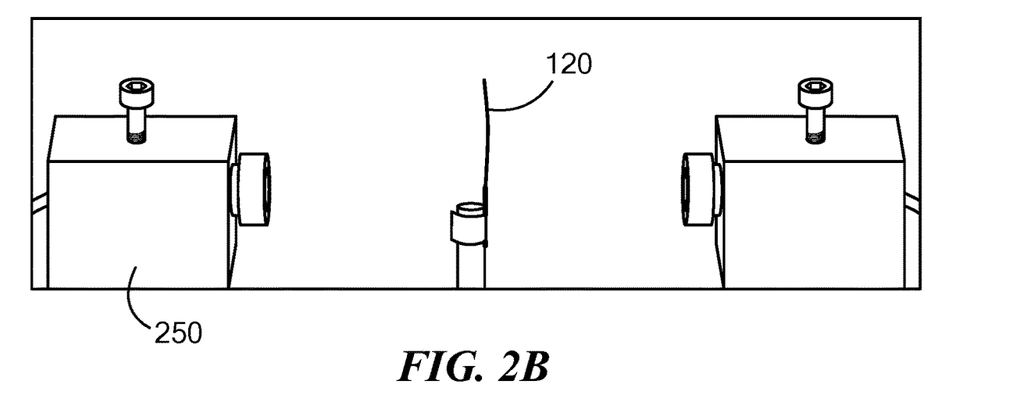
FIG. 2B shows the use of two laser diodes to excite an anisotropic polymer bending actuator in accordance with an embodiment of the present invention.
Figure 5:
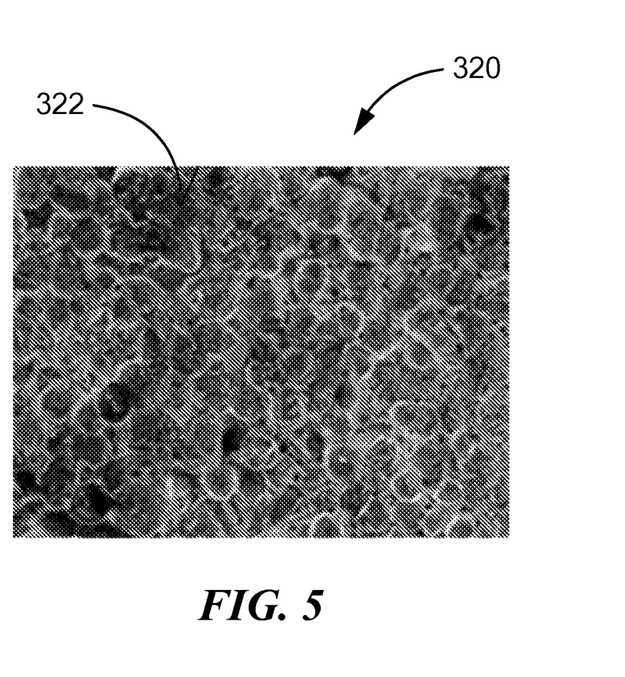
FIG. 5 is an SEM image of a graphene-based thermally conductive coating applied for photo-thermal excitation of an anisotropic polymer bending actuator in accordance with an embodiment of the present invention.

As an example of a method for employing photo-thermal excitation, light absorption at the surface 302 of anisotropic polymer beam 301 may be increased by dip-coating the anisotropic polymer beam 301 with a thermally conductive paint solution, or by other processes for photosorptively treating the surface of the anisotropic polymer beam. In accordance with a preferred embodiment of the present invention, a thermally conductive paint solution 320 was developed from highly thermally conductive graphene flakes 322 as shown in the SEM image of FIG. 5. Beam 301 is then actuated by illumination by one or more sources of light so as to differentially heat surfaces of the anisotropic polymer beam. A source of light for photo-thermal actuation of the anisotropic polymer bending actuator may include one or more high-power laser diodes 250, shown in FIG. 2B. As the term "high-power" is used herein, in reference to a laser diode, "high-power" signifies the optical output of any laser supplying greater than 10 mW of average optical power. In a preferred embodiment of the invention, two 6 W blue (450 nm) laser diodes are used to excite a thin nylon beam (l,w,t: 21.5 mm, 0.7 mm, 112 µm) that has been coated with thermally conductive paint. A nylon bending actuator (l,w,t: 90 mm, 3 mm, 0.87 mm) at input power of 8.15 kW·m$^{-2}$ exhibited less than 5% deterioration in measured transverse displacement amplitude over 100,000 cycles. This relatively long cycle life enables this technology to be used in many applications such as tactile displays, active catheters, dynamic sculptures, toys, optical shutters, and many others.

Since the cooling time constant scales linearly with thickness of the nylon beam, thinner beams provide faster cooling time and, therefore, higher excitation rates.

Thermal conduction across the thickness of the nylon beam scales with the square of the thickness of the nylon beam, thus the bending amplitude reaches steady state faster for thinner thick beams. By exciting the beam with laser diodes at an optical output power of 65 mW, peak-to-peak amplitude of 2.5 mm at 2 Hz is measured.

In some embodiments of the invention, the laser beam heats only a portion of surface 302 of beam 301 (shown in FIG. 3A), in fact the fraction of the area of surface 302 that is radiatively heated may be a small, or even a very small fraction of the area of surface 302 of the beam 301, within the scope of the present invention. This may result in smaller ratios of transverse displacement (transverse to the $\hat{z}$ direction, shown in FIG. 1C) to length l of the beam 302 that are smaller than typically observed with Joule-heated actuators.

Oriented nylon fiber has an anisotropic thermal expansion behavior as evidenced by the fact that it shrinks in length by about 2.5% and expands in thickness by about 4.5% from 25° to 140° C. (The word "oriented," as used herein to describe "fiber," is synonymous with the term "highly-drawn," which is defined above.) The negative thermal expansion coefficient of oriented nylon fiber originates from the fact that amorphous phases of highly drawn polymers such as nylon are energetically less stable than their crystalline phases. Therefore, they can provide large reversible contraction upon accessing conformational entropy when heated.

Figure 6A:
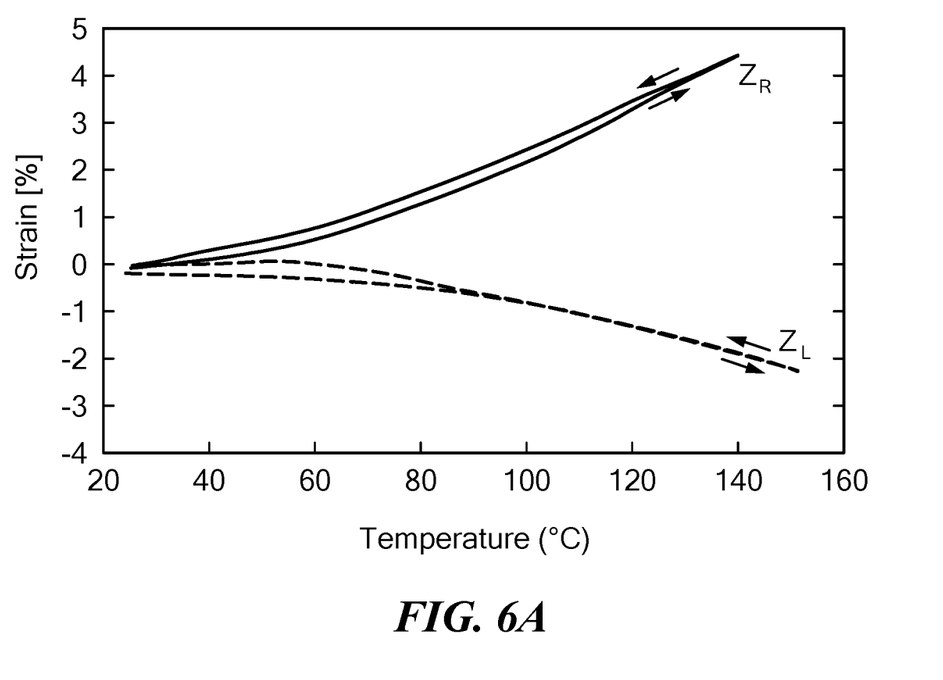
FIG. 6A depicts plots of thermal expansion across the thickness ($\varepsilon_R$) and length ($\varepsilon_L$) of a nylon beam as a function of temperature.

FIG. 6A shows that the lateral thermal expansion coefficient changes non-linearly as a function of temperature from <−2.8×10$^{-5}$ K$^{-1}$ to a large negative thermal expansion coefficient, the absolute value of which, above the glass transition temperature ($T_g$), may exceed 2.8×10$^{-4}$ K$^{-1}$. This negative thermal expansion behavior is a salient phenomenon behind operation of nylon bending actuators within certain embodiments of the present invention. In thermally activated bending actuators, such as thermal bimorphs, there is typically a thermally insulating layer between the top layer and bottom layer to maintain the thermal gradient needed for actuation. The low thermal conductivity of nylon advantageously allows the use of only a single rigid body in embodiment of the present invention, and obviates any thermal insulator layer.

Figure 6B:
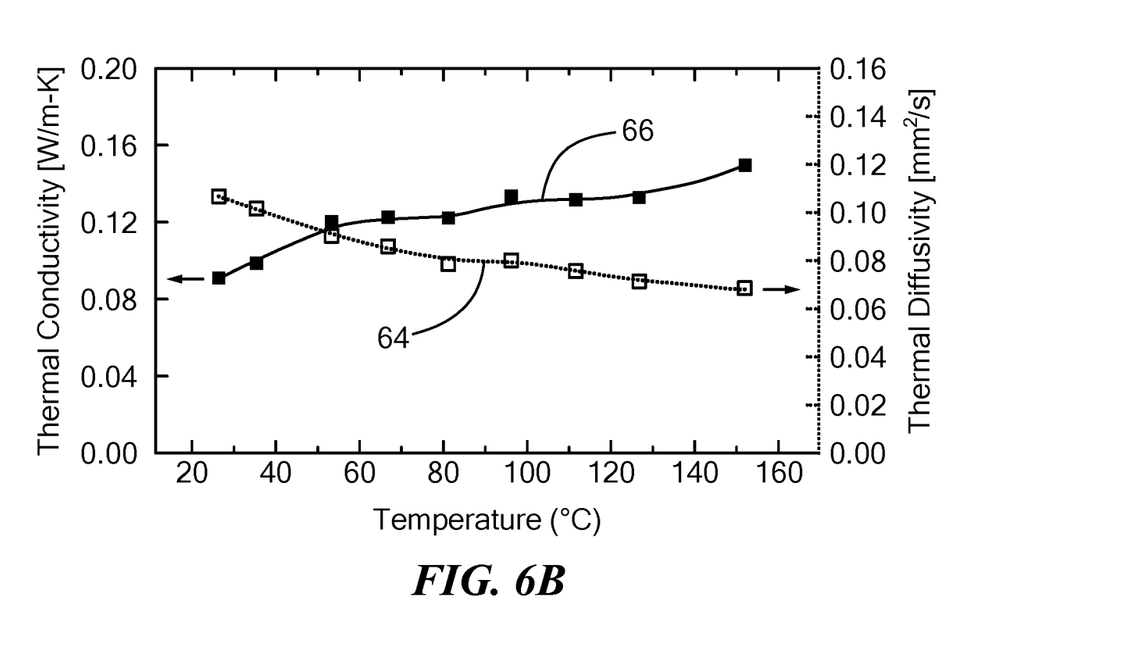
FIG. 6B depicts plots of thermal conductivity and diffusivity of nylon as a function of temperature.

FIG. 6B shows the thermal conductivity 66 and thermal diffusivity 64, each as a function of temperature, of nylon fishing line that is used as precursor material in accordance with a preferred embodiment of the present invention. The thermal conductivity that is ~0.1 W·m$^{-1}$·K$^{-1}$, which is very low when compared with silver (~420 W·m$^{-1}$·K$^{-1}$) for example. Therefore, the heat diffusion time constant, given by $$\tau \sim \frac{t^2}{4\alpha} = \frac{\rho t^2 C_p}{4k},$$

(where t is the thickness, α is the thermal diffusivity, k is the thermal conductivity, ρ is the volumetric mass density, and $C_p$ is the specific heat capacity) is low. More particularly, it takes up to several seconds for the heat to transfer across the thickness of the nylon beam 122. This slow heat transfer rate provides enough time for the heated part to contract and bend the entire nylon beam 122, as shown in FIG. 2A. The concave side 210 of bending actuator 120, may otherwise be referred to herein as the "contracting side." The opposing side 220 of bending actuator 120 bends accordingly.

Another phenomenon that is advantageous to performance of the present invention is the sensitivity of nylon's dynamic modulus to temperature change. By increasing the temperature from 25° to 150° C., the storage modulus (ε') of nylon drops by 88%, making it easier for the contracting side 210 to bend the whole structure. This large drop in the modulus is also responsible for the decay in the blocking force generated at the tip 230 of the actuator 120 at high temperatures.

Figure 6C:
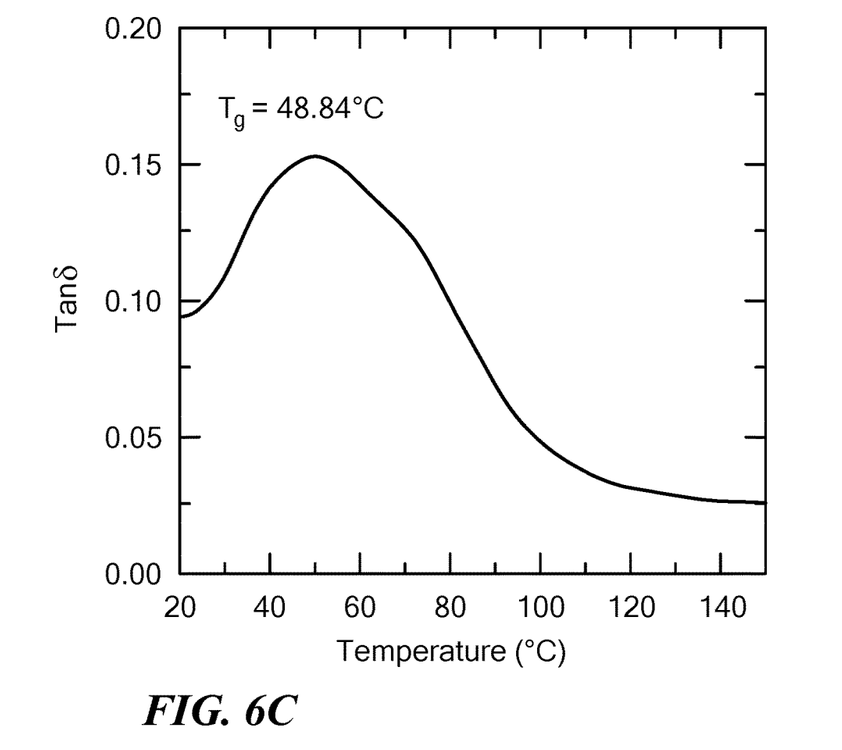
FIG. 6C is a plot of tan $\delta$, where $\delta$ representing the phase lag between stress and strain measured by a dynamic mechanical analyzer, as a function of temperature, for an annealed nylon beam.

FIG. 6C shows a plot versus temperature of tan δ in an annealed nylon beam, where δ is the phase lag between stress and strain. The maximum of the tan δ suggests a glass transition temperature $T_g$ of about 49° C. for the nylon precursor used in a preferred embodiment of the present invention, which is in agreement with the value measured using a differential scanning calorimetry technique.

A fully recoverable symmetric dynamic range of 1.25 (peak-to-peak amplitude transverse excursion normalized to the length of the actuator) was measured at an input power density of 19.4 kW·m$^{-2}$ (or mW·mm$^{-2}$), close to the theoretical limit of 1.2732 (i.e., 4/π) for bending actuators.

Figure 7:
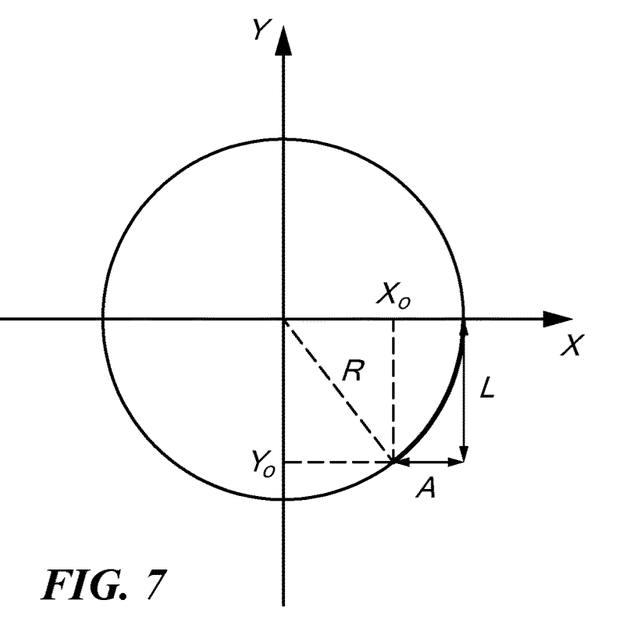
FIG. 7 depicts general geometry of a bending actuator.

The theoretical limit for the dynamic range of transverse displacement amplitude is readily appreciated by reference to FIG. 7. From the equation of a circle, the square of the radius R is related to orthogonal radii as:

$$R^2 = (R-A)^2 + L^2,$$

from which it follows that $$R = \frac{A^2 + L^2}{2A}.$$

The amplitude A attains its maximum value when the actuator bends to form a semi-circle. The radius of curvature, R, in this case is A/2. Therefore, the theoretical limit for the normalized dynamic range (peak-to-peak transverse displacement amplitude over length) is:

$$\tilde{A}_{pp} = 2\frac{A}{\pi R} = \frac{4}{\pi}.$$

A reversible radius of curvature of 53.6 mm was achieved from the nylon bending actuator described above, which agrees with model calculations, described below, for temperatures of approximately 96° C. This radius of curvature is smaller than the 83.3 mm reported for spongy graphene based bimorph actuators, but larger than the 10 mm that has been reported for trilayer electroactive conducting polymer actuators. A radius of curvature of 21.6 mm was achieved at input power of 21.55 kW·m$^{-2}$, but the nylon beam slightly deformed permanently in shape. For a temperature range of 25° to 150° C., the model described below provides a lower bound of 16.2 mm for the radius of curvature.

Catch-State

During an annealing process, nylon shrinks in length by up to 25%. Annealing is typically performed for a sufficient time for dimensional stability to be achieved. As the annealing temperature is decreased from 150° to 60° C., the reversibility of the actuation motion also decreases. In other words, the polymer bending actuator 120 tends to stay at its location after turning the actuator off, i.e., when no further thermal input is applied. This is analogous to the 'catch-state' that some biological muscles such as mollusks have. Catch-state or lock-state occurs when muscle locks at its current length without consuming energy.

Figure 8A:
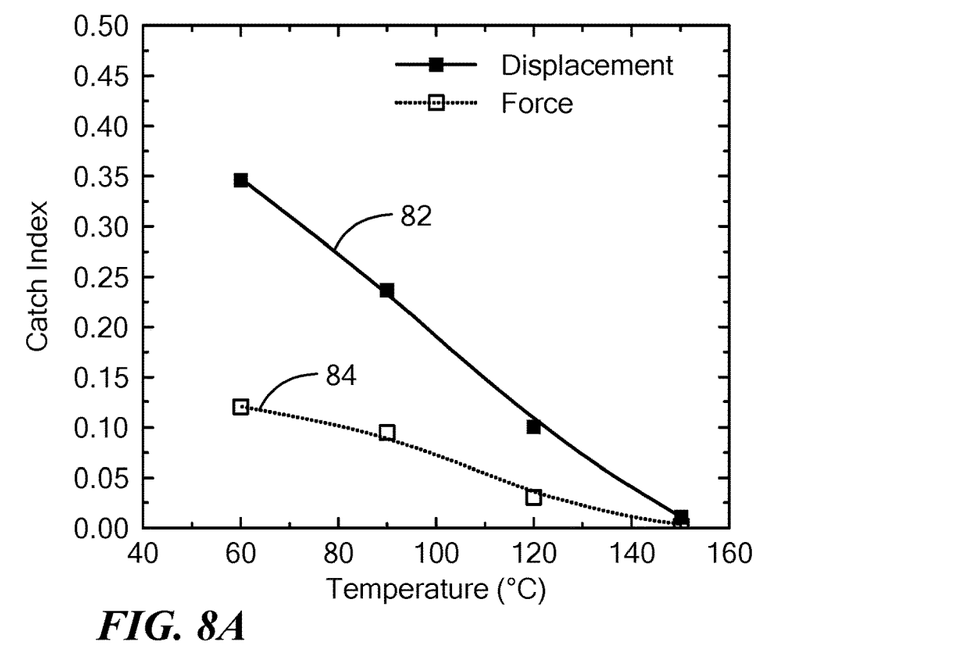
FIG. 8A shows plots catch index, as defined below, for the displacement and force of a bending actuator in accordance with the present invention, as a function of annealing temperature.
Figure 8B:
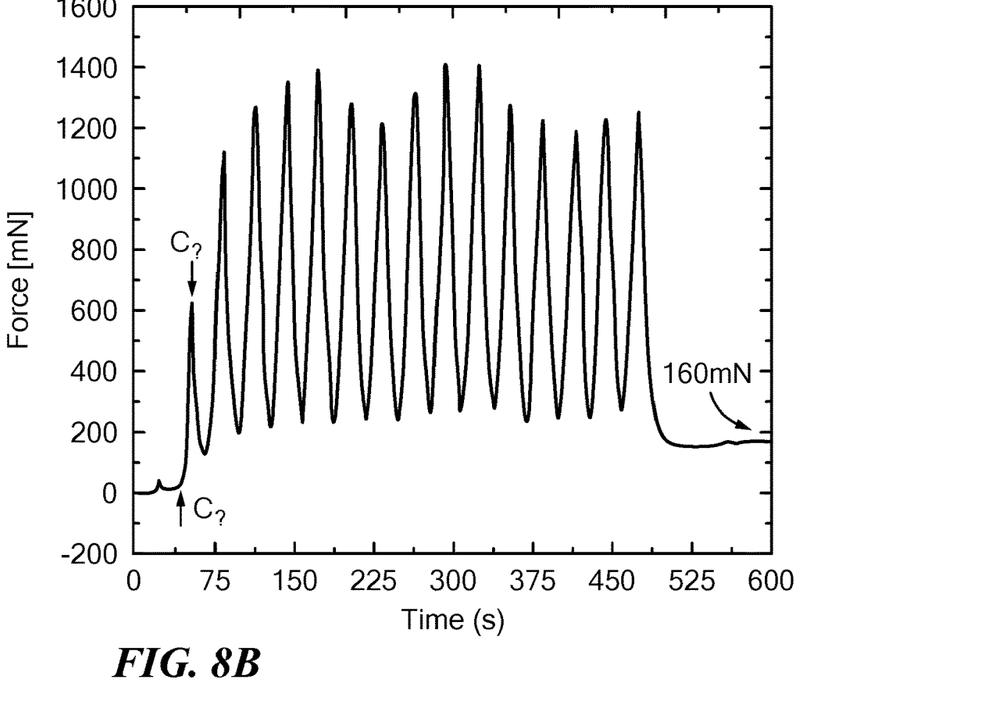
FIG. 8B illustrates a catch index of approximately 0.12 as force is plotted as a function of time for successive activations of an anisotropic polymer.

Referring now to FIG. 8A, a linear correlation is obtained between the annealing temperature and the ratio of the locked displacement amplitude 82 or force 84 to the corresponding active amplitude/force, referred to hereinafter as the "catch-index". This 'catch-state' happens when the temperature of the muscle is increased to a point higher than the temperature at which the muscle was annealed. In the long run, over multiple cycles during actuation, the muscle may anneal, thereby reducing the catch-index. This problem of temporary catch-state can be resolved by designing a locking mechanism. But if, for applications such as active catheters, having a catch-state for only several cycles is desirable, cost of nylon is cheap enough to avoid adding any accessories to obtain a permanent catch-state. As FIG. 8B indicates, an anisotropic polymer bending actuator in accordance with an embodiment of the present invention has been found to hold approximately 160 mN out of the 1400 mN peak force it generated in the active state. Bending actuator 120 may be returned to its neutral position by applying heat to the cooler of the opposing faces of the actuator.

In accordance with certain embodiments of the invention, annealing is performed at a temperature between 20° C. above glass temperature of the anisotropic polymer and 20° C. below melting point of the anisotropic polymer, in such a manner as to create a catch state at a specified fractional amplitude of bending. More particularly, annealing the beam of anisotropic polymer is preferably performed at a temperature between 60° C. and 150° C.

Figure 9:
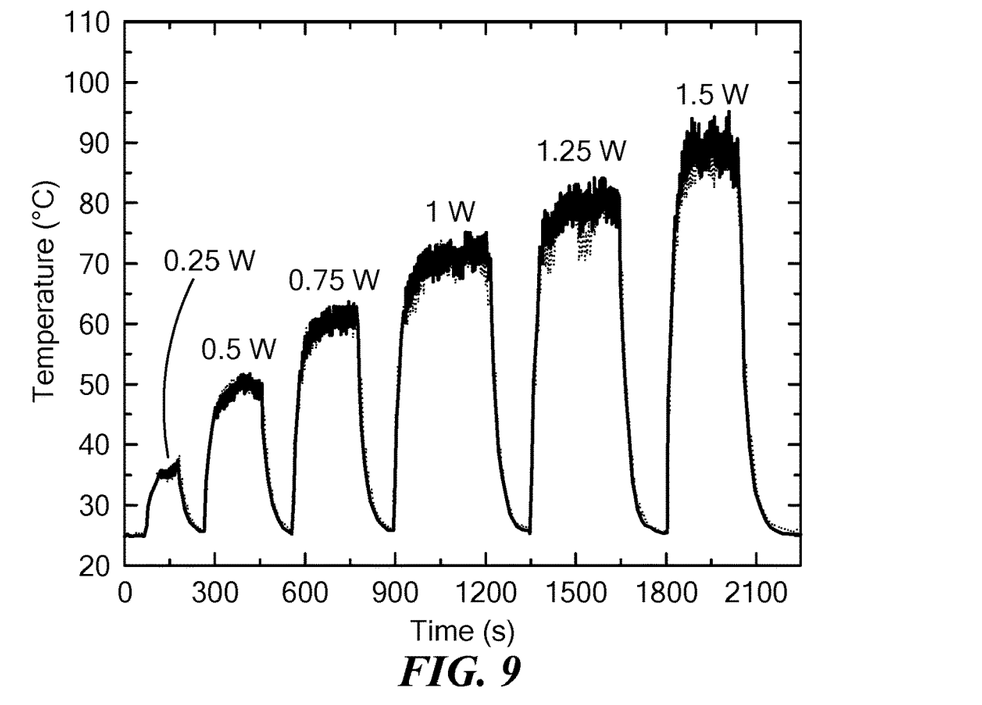
FIG. 9 plots temperature as a function of time for a bending actuator excited at constant power with a continuous square wave input signal, as further discussed in the Description below.

In accordance with certain embodiments of the present invention, input thermal power may be supplied in alternation between two opposing sides of a polymer bending actuator 120. In that case, the surface temperature of the actuator increases until it reaches a plateau which, itself, is a function of power. Similarly, the amplitude of displacement of the actuator tip also grows over several cycles until it reaches a plateau, as shown in FIG. 9. At the plateau, a temperature gradient of around 3° C. keeps the beam actuating. This temperature gradient is small compared to the thermal gradient required for phase transition materials such as VO$_2$, where a thermal gradient of ΔT ~15° C. is required. It should be noted that, for very long pulses, the amplitude of displacement can reach the plateau within even one cycle. Full reversibility of amplitude response is desirable in that it provides for controlling the position of the actuator's tip without using any position sensors.

Aside from the transverse displacement performance that has been described, a nylon bending actuator 120 in accordance with the present invention may also generate a substantial blocking force, even at only 12% of the storage modulus value at room temperature. The storage modulus is the fraction of energy stored within the actuator under dynamic excitation, i.e., the ratio of stress to strain times the cosine of the phase lag δ between stress and strain, as defined above.

As the term is used herein, a "normalized force" refers to a force times the length of the bending actuator divided by the actuator width and the square of its thickness. Normalized forces of up to 7.5 MPa (fully recoverable, with no catch, where a catch state has been discussed above) have been achieved, and normalized forces as great as 55 MPa, with a catch index of 0.12, have been achieved from bending actuators in accordance with the present invention.

Figure 10:
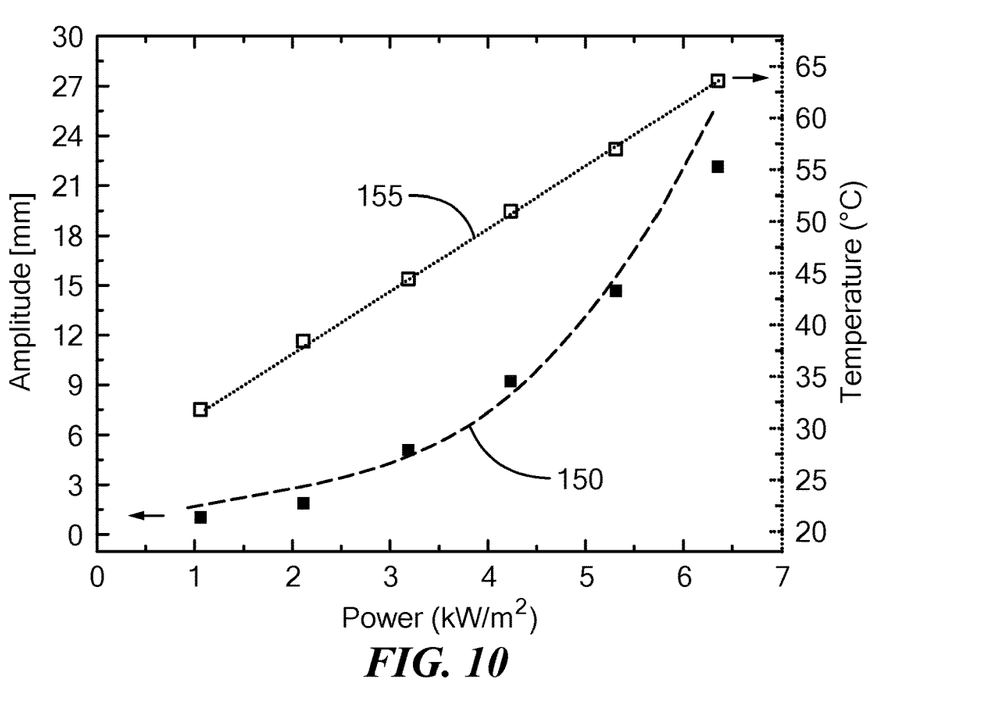
FIG. 10 shows plots of transverse displacement amplitude and temperature versus input power for a bending actuator in accordance with an embodiment of the present invention. Temperatures are fit to a line, and displacement amplitudes compared with a model described below.

To explain the behavior of the anisotropic polymer bending actuator 120, a mathematical model that relates the length of the actuator and other parameters to the displacement at the tip of the actuator is described as follows:

$$\delta = -\alpha_T \frac{\Delta T}{2h_T} L^2,$$

where $\alpha_T$ is the temperature-dependent coefficient of thermal expansion, $\Delta T$ is the difference between the temperature at the surface of the actuator (T) and the initial temperature ($T_i$), $h_T$ is the thickness of the actuator which is temperature-dependent, and L is the length of the actuator. Since $\alpha_T$ is temperature-dependent, the displacement at the tip of the actuator is non-linear with respect to the temperature change. By using the values measured for the thermal expansion coefficients and the slope of the temperature vs. power relationship, it becomes possible to predict the value of the amplitude as a function of temperature. FIG. 10 plots experimental displacement amplitude data and modeled results 150 as well as temperature and a linear fit 155 thereto, measured using an anisotropic polymer bending actuator 120 in accordance with an embodiment of the present invention.

Fabrication Procedure

Depending on the required thickness and width of the bending actuator 120 to be fabricated in accordance with the present invention, precursor monofilament materials are preferably chosen from the following table, provided by way of example, and without limitation:

List of the precursors used in the bending actuator design.

| Material Name | Diameter (mm) | Coating | Stimulus |
|---|---|---|---|
| Sufix Superior 650 lb | 2.40 | Ag/Nb paint | Joule heating |
| Sufix Superior 200 lb | 1.40 | Ag/Nb paint | Joule heating |
| Sufix Superior 60 lb | 0.70 | Ag/Nb paint | Joule heating |
| The Thread Exchange MON012CLR04S | 0.30 | Graphene paint | Photo-excitation |

Sufix is a brand of Rapala VMC Corporation of Helsinki, Finland. The raw nylon filaments are pre-annealed at 60° C. for two hours to make them straight and easy to handle during a roller-pressing process. Nylon beams with rectangular cross section were made by roller-pressing the pre-annealed nylon filaments using a rolling mill device (Durston DRM 130). To make square cross section filaments, the pre-annealed nylon filaments were pressed through the V grooves of the rolling mill. After the roller-pressing process, the nylon beams with rectangular cross section were clamped between two very flat aluminum bars and were annealed at 150° C. (below the melting point) for two to three hours. For nylon square rods, they were place inside a metallic square pipe. After the annealing process, the nylon beams were cut into the desired lengths and were masked with a very thin piece of scotch tape in the middle of their top and bottom surfaces. This masking provides for application of loop 124 (shown in FIG. 2A) of Joule heating path that starts and ends at one end of the beam 122. Conductive paint may then be applied on the surfaces 210, 220 of the anisotropic polymer bending actuator 120. All of the coated surfaces should be electrically isolated from each other.

Conductive Paint

In accordance with one embodiment of the invention, SPI flash-dry silver colloidal suspension, supplied by SPI Supplies of West Chester, Pa., is used as the base material for the conductive paint used as a Joule heating element for the anisotropic polymer bending actuators 120. This conductive paint is made of silver flakes suspended in an adhesive resin. Layers of this colloidal suspension (also referred to herein as an "ink" or "silver paint"), preferably ranging in thickness between 40-50 are applied. In high bending curvatures the flakes can slide over each other and maintain continuity of a conductive path. Other conducting nanowires may also be employed within the scope of the present invention. The aforesaid conductive paint provides a conductivity of approximately 60 k$\Omega \cdot m^{-2}$, normalized to the surface area of the actuator, although all heating modalities are within the scope of the present invention, as discussed. For example, Joule heating may be achieved by applying current to nichrome wire applied to the surface of anisotropic polymer beam 122.

Figure 1C:
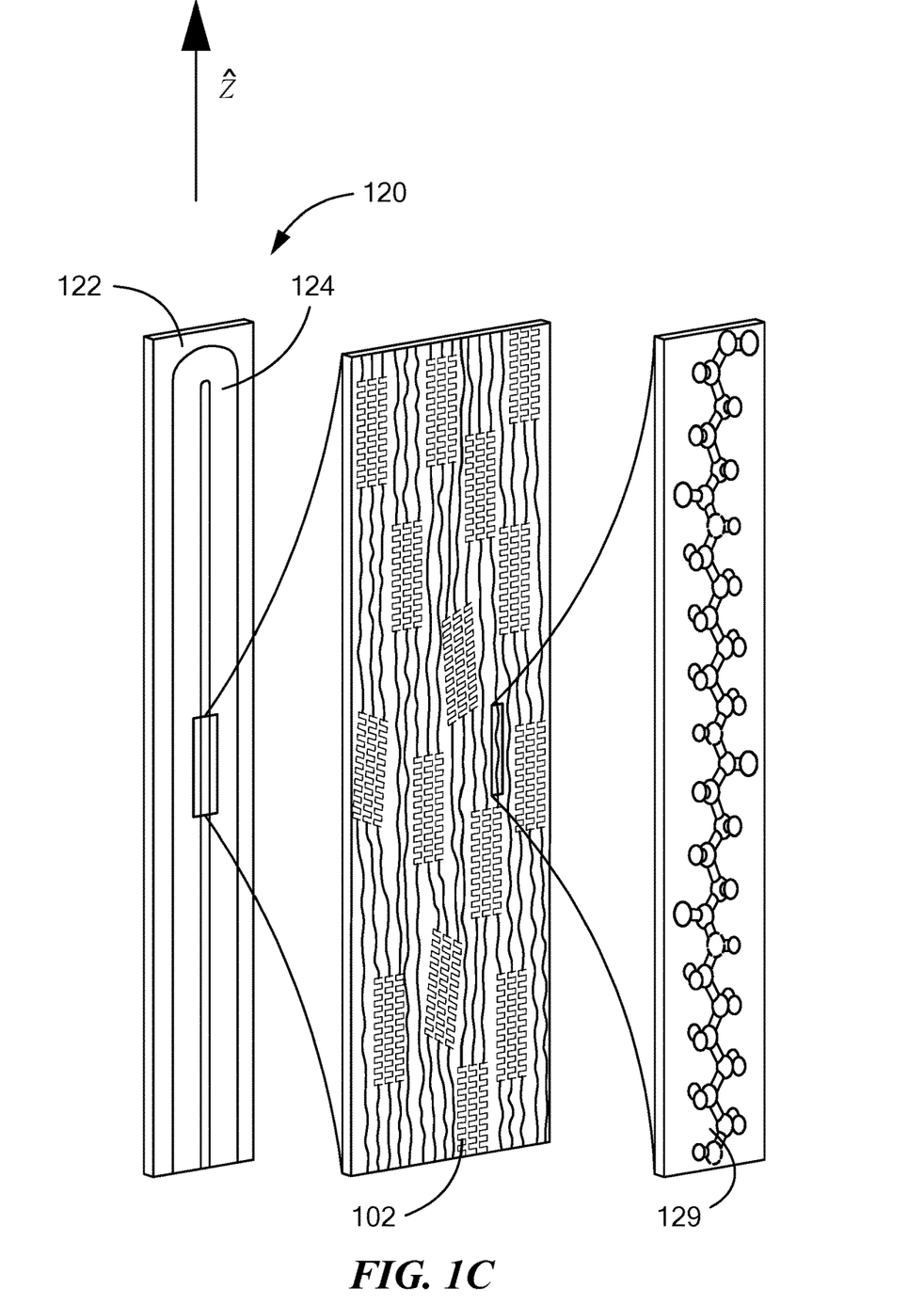
FIG. 1C schematically depicts a nylon bending actuator with conductive traces on its surface; with zoomed-in illustrations showing highly aligned crystalline regions of the nylon beam, and the molecular structure of nylon 6,6.

As mentioned above, a temperature gradient is to be maintained across the thickness of the anisotropic polymer beam 122 (shown in FIG. 1C). The thickness t of beam 122 and the ambient temperature (in a passive cooling setup) are two of the parameters that can affect the bending amplitude. By decreasing the temperature gradient, the bending actuator turns into a linear actuator which can create large amount of force and very small displacement orthogonal to the axis of the actuator.

To compensate for any variations in resistance of the Joule heating traces during the actuation or the fabrication process, the applied voltage is preferably controlled by a proportional-integral-derivative (PID) controller to ensure that a constant power is delivered to respective sides of the actuator during actuation. In accordance with an alternate embodiment of the invention, the resistance of Joule heating trace 124 may be monitored as a measure of transverse displacement of the anisotropic polymer bending actuator 120.

By cycling the input power, we observed a fully reversible amplitude response. This reversibility is very helpful in controlling the position of the actuator's tip without using any position sensors.

Multidirectional Motion

Figure 11:
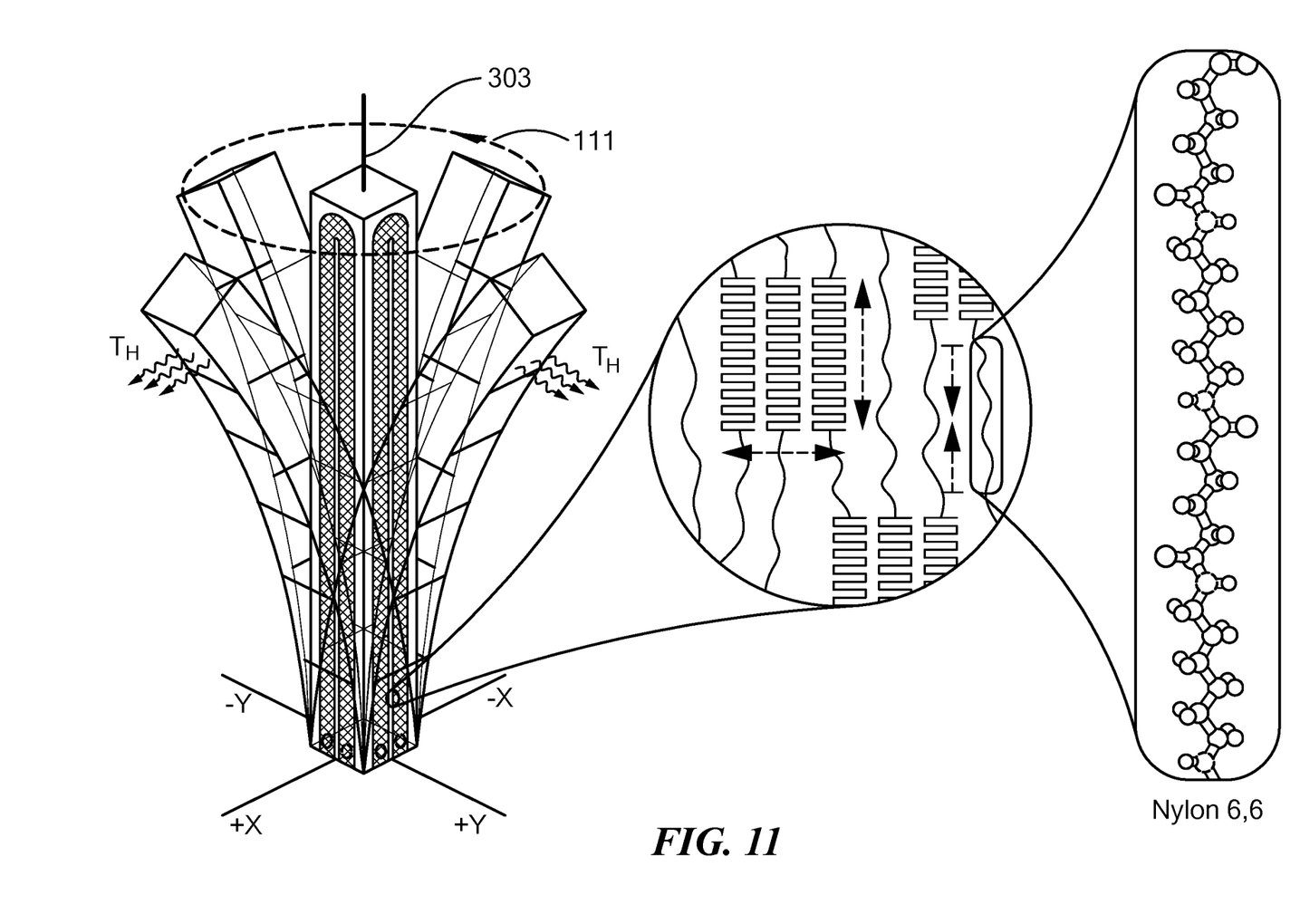
FIG. 11 depicts operation of a multidirectional bending actuator in accordance with an embodiment of the present invention, with zoomed-in illustrations showing highly aligned crystalline regions of the nylon beam, and the molecular structure of nylon 6,6 polymer.

Referring now to FIG. 11, roller-pressing nylon monofilament feedstock through V grooves of a rolling mill provides for fabrication of nylon square rods 303. Following the same fabrication procedure as for the bending actuator 120, shown in FIG. 1C, four Joule heating traces of conductive paint are applied. When power is applied to each sides of the actuator, bending may be achieved in ±X, ±Y and even −Z directions when all of the four sides of the rod are excited at the same time. To provide each sides of the actuator with variable voltages, a half-bridge rectifier made of Schottky diodes may be employed. By applying two sinusoidal signals 90° out of phase to the opposite sides of the actuator (top and bottom connected to $V_o \sin(\omega \cdot t)$, left and right connected to $(V_o \sin(\omega \cdot t + \pi/2))$ the actuator's tip may be driven in a circular path 111. Similarly, by applying two triangle signals with a phase difference of 90°, the actuator tip may be driven in a square path. When two sinusoidal waves with one having double the frequency of the other one and a relative phase of 90° are applied, more complex trajectories such as Lissajous figures may be generated.

Frequency Response

The frequency response of the anisotropic polymer bending actuators may be controlled, within the scope of the present invention, by adjusting dimensions. The natural frequency of a cantilever beam is given by:

$$\omega_n \sim \frac{t}{L^2}\sqrt{\frac{E}{\rho}},$$

where t is the thickness of the actuator, L is the length of the beam, E is Young's modulus, and ρ is the volumetric mass density.

Applications

A minimum force of 30-50 mN provides effective stimulation of human mechanoreceptors in order to give us sense of touch. The force generated by nylon bending actuators satisfies this requirement. In addition to this, the relatively good response time of the actuator makes it suitable for use in the design of a tactile display, within the scope of the present invention. Due to the geometry and functionality of the nylon multidirectional actuator, it may be used to navigate through blood vessels or other internal organs. The key requirements for navigating through blood vessels are small diameter (<1.65 mm), a high degree of bending (>20°), a high enough force (~25 mN at the tip), and adequate response time (on the order of seconds), all of which are satisfied by nylon bending actuators in accordance with the present invention. In a vascular propulsion embodiment, the actuator is coupled to a particle, and a controller adapted to activate the heating element drives the actuator to apply a force for propelling the particle through a lumen, for example.

The embodiments of the invention described above are intended to be merely exemplary; numerous variations and modifications will be apparent to those skilled in the art. All such variations and modifications are intended to be within the scope of the present invention as defined in any appended claims.

The following concepts are taught herein and reserved to be claimed in the future:

1. A bending actuator comprising:
   a. a beam of anisotropic polymer material characterized by a greater degree of molecular orientation along a longitudinal axis than transverse to the longitudinal axis, and by a substantially polygonal-cross section taken in any plane transverse to the longitudinal axis; and
   b. a heating element in thermal contact with at least one of a pair of opposing faces parallel to the longitudinal axis of the beam of anisotropic polymer material.
2. A bending actuator in accordance with concept 1, wherein the anisotropic polymer is nylon.
3. A bending actuator in accordance with concept 1, wherein the substantially polygonal cross section is substantially rectangular.
4. A bending actuator in accordance with concept 1, wherein a distinct Joule heating element is in thermal contact respectively with each of two opposing faces of the beam of anisotropic polymer material.
5. A method for applying a force transverse to a longitudinal axis of an actuator, the method comprising:
   a. providing a beam of anisotropic polymer characterized by a greater degree of molecular orientation along a longitudinal axis than transverse to the longitudinal axis, and by a substantially polygonal-cross section taken in any plane transverse to the longitudinal axis;
   b. applying a heating element to at least one of a pair of opposing faces parallel to the longitudinal axis of the beam; and
   c. causing bending of the beam by differentially heating at least a first face of the pair of opposing faces with respect to a second face of the pair of opposing faces by Joule heating.
6. A method in accordance with concept 5, wherein the anisotropic polymer is nylon.
7. A method in accordance with concept 5, wherein forming the beam includes roller-pressing the anisotropic polymer.
8. A method in accordance with concept 5, wherein the substantially polygonal cross section is substantially rectangular.
9. A method in accordance with concept 5, wherein applying a Joule heating element to at least one face includes applying a Joule heating element to two opposing faces of the beam of anisotropic polymer.
10. A method of manufacture of a bending actuator, the method comprising:
    a. forming a beam of anisotropic polymer characterized by a greater degree of molecular orientation along a longitudinal axis than transverse to the longitudinal axis, and by a substantially polygonal-cross section taken in any plane transverse to the longitudinal axis; and
    b. applying a Joule heating element to at least one of a pair of opposing faces parallel to the longitudinal axis of the beam.
11. A method in accordance with concept 10, wherein the anisotropic polymer is nylon.
12. A method in accordance with concept 10, wherein forming the beam includes roller-milling the anisotropic polymer.
13. A method in accordance with concept 10, wherein the substantially polygonal cross section is substantially rectangular.
14. A method in accordance with concept 10, wherein applying a Joule heating element to at least one face includes applying a Joule heating element to two opposing faces of the beam of anisotropic polymer.
15. A method in accordance with concept 10, wherein applying a Joule heating element to at least one face includes applying a conductive paint to the at least one face.
16. A method in accordance with concept 10, wherein applying a Joule heating element to at least one face includes applying nichrome wire to the at least one face.

We claim:

1. A method for applying a force transverse to a longitudinal axis of an actuator, the method comprising:
   a. providing a beam of anisotropic polymer characterized by a greater degree of molecular orientation along a longitudinal axis than transverse to the longitudinal axis, and by a substantially polygonal-cross section taken in any plane transverse to the longitudinal axis;

b. providing a heat source; and c. causing bending of the beam by using the heat source to differentially photothermally heat at least one face of a pair of opposing faces of the beam with respect to a second face of the pair of opposing faces.

2. A method in accordance with claim 1, wherein the heat source is light.

3. A method in accordance with claim 1, wherein the heat source is a laser.

4. A method in accordance with claim 3, wherein differentially photothermally heating at least one face includes irradiating a first face with a first laser and a second face with a second laser.

5. A method in accordance with claim 1, wherein the beam exhibits a catch state, further comprising returning the actuator to a neutral condition by applying heating to the cooler of the opposing faces.

6. A method of manufacture of a bending actuator, the method comprising:

a. forming a beam of anisotropic polymer material polygonal-cross section; and b. photosorptively treating at least one of opposing faces of the beam of anisotropic polymer.

7. A method in accordance with claim 6, wherein photosorptively treating includes applying a coating of thermally conductive paint solution.

8. A method in accordance with claim 7, wherein the thermally conductive paint solution includes thermally conductive graphene flakes.

9. A method of manufacture of a bending actuator, the method comprising:

a. providing a beam of anisotropic polymer characterized by a greater degree of molecular orientation along a longitudinal axis than transverse to the longitudinal axis, and by a substantially polygonal-cross section taken in any plane transverse to the longitudinal axis;

b. annealing the beam of anisotropic polymer at a temperature between 20° C. above glass temperature of the anisotropic polymer and 20° C. below melting point of the anisotropic polymer in such a manner as to create a catch state at a specified fractional amplitude of bending; and c. treating at least one face of the beam for thermal activation.

10. A method in accordance with claim 9, wherein annealing the beam of anisotropic polymer is at a temperature between 60° C. and 150° C.

11. A method in accordance with claim 9, wherein providing the beam of anisotropic polymer includes roller-pressing a length of anisotropic polymer filament through a rolling mill.

12. A method in accordance with claim 9, wherein treating the at least one face of the beam includes depositing a conductive trace for Ohmic heating.

13. A method in accordance with claim 9, wherein treating the at least one face of the beam includes photosorptive treatment.

14. A method in accordance with claim 9, wherein treating the at least one face of the beam includes applying heating traces to a plurality of distinct pairs of faces to achieve multidirectional actuation.

15. A method in accordance with claim 14, wherein the plurality of distinct pairs of faces of the beam are substantially orthogonal to each other.

* * * * *